United States Patent [19]

Jansen et al.

[11] 4,140,110

[45] Feb. 20, 1979

[54] SYSTOLIC PRESSURE DETERMINING APPARATUS AND PROCESS USING INTEGRATION TO DETERMINE PULSE AMPLITUDE

[75] Inventors: William D. Jansen, Palo Alto; Jerry D. Haney, Sunnyvale, both of Calif.

[73] Assignee: American Optical Corporation, Southbridge, Mass.

[21] Appl. No.: 754,201

[22] Filed: Dec. 27, 1976

[51] Int. Cl.$^2$ .............................................. A61B 5/02
[52] U.S. Cl. ........................... 128/2.05 A; 128/2.05 M
[58] Field of Search ................. 128/2.05 A, 2.05 C, 128/2.05 D, 2.05 E, 2.05 G, 2.05 F, 2.05 M, 2.05 S, 2.05 P, 2.05 V, 2.05 Q, 2.05 Z

[56] References Cited

U.S. PATENT DOCUMENTS

| | | | |
|---|---|---|---|
| 3,598,112 | 8/1971 | Figar | 128/2.1 R |
| 3,835,840 | 9/1974 | Mount | 128/2.05 V |
| 3,871,360 | 3/1975 | Van Horn et al. | 128/2.05 R |
| 3,878,833 | 4/1975 | Arneson et al. | 128/2.05 A |
| 3,996,925 | 12/1976 | Djordjevich | 128/2.05 V |
| 4,009,709 | 3/1977 | Link et al. | 128/2.05 A |
| 4,035,622 | 7/1977 | Obermajer | 235/151.3 |

FOREIGN PATENT DOCUMENTS 149183  7/1961  U.S.S.R. ................. 128/2.1 R

*Primary Examiner*—Robert W. Michell
*Assistant Examiner*—Francis J. Jaworski
*Attorney, Agent, or Firm*—Jeremiah J. Duggan; Stephen A. Schneeberger; Howard R. Berkenstock, Jr.

[57] ABSTRACT

In systolic pressure determining apparatus utilizing a pressure cuff and means for measuring a fluctuating quantity proportional to the sum of the cuff pressure and the fluctuating component proportioned to the pulsatile blood pressure, and including means for determining the maximum value of the fluctuating component as cuff pressure is varied, the improvement comprising means for converting the quantity into a representation of a time derivative of the fluctuating component means for obtaining the time integral of the time derivative over an interval of predetermined limits between initiation of systolic rise and systolic peak in each blood pressure pulse, and means extending the time integral, as a measure of pulse pressure amplitude, to the maximum value determining means. Specifically, certain crossings of a reference value by the time derivative are recognized as being the initiation of systolic rise and the systolic peak respectively, and the integration occurs over this interval.

The method implemented by the improved means also comprises an aspect of the invention.

9 Claims, 13 Drawing Figures

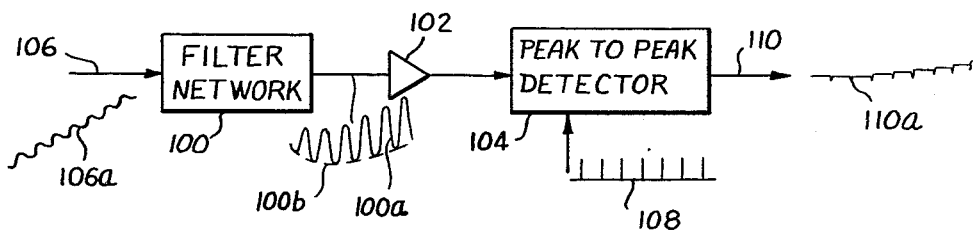
Fig. 1 (PRIOR ART)
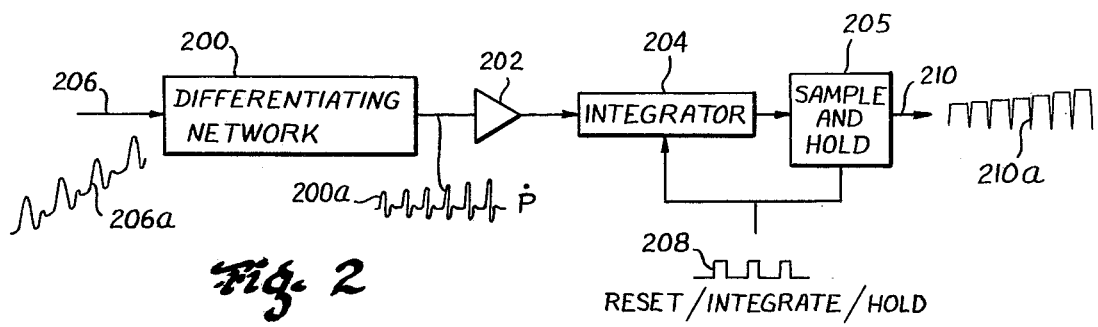
Fig. 2
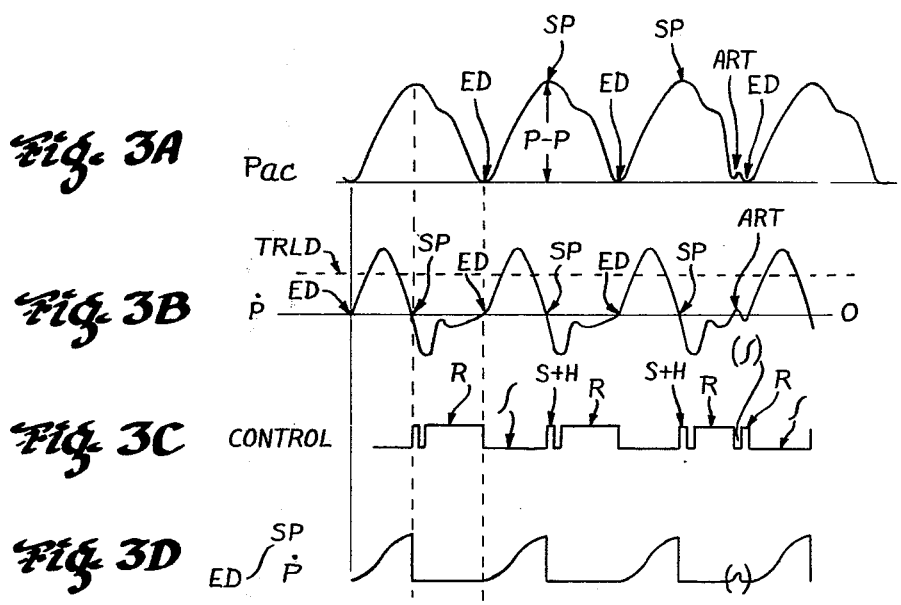
Fig. 3A
Fig. 3B
Fig. 3C
Fig. 3D
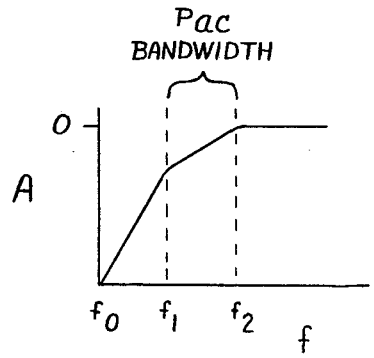
Fig. 5

SYSTOLIC PRESSURE DETERMINING APPARATUS AND PROCESS USING INTEGRATION TO DETERMINE PULSE AMPLITUDE

BACKGROUND OF THE INVENTION

The present invention relates generally to the field of blood pressure monitoring, and more particularly to automatic monitoring of systolic blood pressure.

The prior art is replete with devices for measuring systolic pressure of a living subject. An old and simple device is a pressurizeable cuff used in combination with a mercury manometer which reads pressure in the cuff and a stethoscope which is used to listen to Korotkof sounds. In another advanced method of measuring blood pressure, the distance from a blood pressure cuff to the wall of an artery is accurately determined by measuring Doppler shifts of sound waves reflected by the artery. In yet other methods for measuring blood pressure intrusive devices are often inserted directly into blood vessels.

Oscillometric methods of determining systolic pressure are also well known in the art. In such methods, the operator observes the representation of the strength of pulsations of pressure within an artery. This can be done visually, as by watching the extent of bouncing at the top of a mercury column in a mercury manometer which is in pressure communication with the cuff or indirectly as by measuring the occlusion which occurs to a blood vessel in the pinna of the ear as pressure is exerted thereon. These oscillometric methods generally define systolic pressure to be the maximum applied pressure with which threshold oscillations are observed to occur. With a typical mercury manometer and pressurized cuff, this pressure would then be the highest pressure which the operator noted bouncing on the top of the mercury column as the pressure in the cuff was slowly and relatively uniformly reduced. However there are inaccuracies associated with this method for determining threshold oscillations, since the inertia of the mercury column does not allow it to noticeably respond to narrow width pressure pulses.

Each of the aforementioned techniques or devices for measuring systolic pressure exhibit some form of shortcoming such as inaccurate response to narrow width pressure pulses or the requirement for sophisticated and/or expensive measuring equipment.

There is described in U.S. Patent Application Ser. No. 578,047, filed May 15, 1975 by Link et al for Apparatus and Process for Determing Systolic Pressure, assigned to the present assignee and incorporated herein by reference, a method and apparatus for automatically and relatively simply obtaining accurate systolic blood pressure measurements, thereby overcoming the shortcomings of the aforementioned devices. That device determines systolic pressure by applying pressure to a living test subject by changing pressure in a pressure cuff attached to the subject adjacent a blood vessel; by measuring at the cuff a quantity proportional to a time dependent fluctuating component representative of the pulsatile pressure within the blood vessel, which quantity is proportional to the amplitude of the pulsatile pressure; by determining the maximum value attained by the quantity as the applied pressure is changed; by storing a representation of the maximum value; by determining when the quantity is substantially equal to about one half of the maximum value for an applied pressure greater than the pressure applied with the maximum value occurs or results; and by reading out the applied pressure corresponding to the quantity being substantially equal to about one half of the maximum value, the read out pressure corresponding to the systolic pressure of the subject. The signal from the pressure cuff comprises a fluctuating quantity proportional to a sum, that sum comprising a time dependent fluctuating component proportional to the amplitude of the pulsatile pressure within the blood vessel, which component has a steeply rising wavefront between end diastole and systole, plus the selectively changeable pressure applied externally adjacent the blood vessel by the cuff.

In the apparatus of the aforementioned application U.S. Ser. No. 578,047, the signal from the pressure cuff is applied to a filtering network to remove the effects of the cuff pressure ramp. The resulting oscillating signal is considered to be proportional to the amplitude of the pulsatile pressure within the blood vessel and a peak-to-peak detector then makes amplitude measurements utilized to complete the signal processing. However, random and uncontrollable deviation from the presumed linearity of the pressure ramp may introduce errors in this amplitude determination. If a large perturbation in the cuff pressure ramp is encountered, the filter requires a considerable time to recover and may allow some variation in the base line from which the fluctuating signal proportional to the amplitude of the pulsatile pressure within the blood vessel is measured, thereby resulting in an erroneous output from the peak-to-peak detector.

The present invention provides a solution to the problems associated with occasional perturbations in the applied pressure ramp of the cuff in a systolic blood pressure monitor of the type described in the aforementioned U.S. patent application Ser. No. 578,047.

SUMMARY OF THE INVENTION

In one sense, the invention comprises an improvement in apparatus for the determination of systolic pressure of a living test subject, comprising: a pressure cuff for applying a selectively changeable pressure to the test subject adjacent a blood vessel; transducer means for measuring a fluctuating quantity proportional to a sum, the sum comprising a time dependent fluctuating component proportional to the amplitude of the pulsatile pressure within the blood vessel plus the selectively changeable pressure applied by the cuff externally adjacent to blood vessel; means for determining the maximum value attained by the fluctuating component as the applied pressure is changed; means for storing the representation of the maximum value; means for determining when the fluctuating component is substantially equal to a predetermined fraction of the maximum value for an applied pressure greater than the pressure applied when the maximum value results; and means for reading out the applied pressure corresponding to the fluctuating component being substantially equal to said predetermined fraction of the maximum value, the readout pressure corresponding to the systolic pressure of the subject and wherein the improvement specifically comprises:

Means for converting the fluctuating quantity into a representation of a time derivative of the fluctuating component thereof; means for obtaining the time integral of the time derivative representation over an interval of predetermined limits in each of successive blood pressure pulses, the predetermined intervals of integration occurring between initiation of systolic rise and the systolic peak in respective blood pressure pulses, each of the integrals being proportional to the amplitude of the pulsatile pressure for the respective pulse; and means for extending the time integral representations to the maximum value determining means.

In another sense, the invention comprises an improved process, or method, for determining systolic pressure comprising: applying pressure to a living test subject by changing pressure in a pressure cuff attached to the subject adjacent a blood vessel; measuring at the cuff a quantity proportional to a sum, the sum comprising a time dependent fluctuating component proportional to the amplitude of the pulsatile pressure within the blood vessel plus the selectively changeable pressure applied by the cuff externally adjacent the blood vessel; determining the maximum value attained by the fluctuating component as the applied pressure is changed; storing a representation of the maximum value; determining when the fluctuating component is substantially equal to a predetermined fraction of the maximum value for an applied pressure greater than the pressure applied when the maximum value results; and reading out the applied pressure corresponding to the fluctuating component being substantially equal to said predetermined fraction of the maximum value, the readout pressure corresponding to the systolic pressure of the subject and wherein the specific improvement comprises the steps of: converting the quantity proportional to the sum into a representation of a time derivative of the fluctuating component thereof:

determining the time integral of the time derivative representation over an interval of predetermined limits in each of successive blood pressure pulses, the predetermined interval of integration occurring between initiation of systolic rise and the systolic peak in respective blood pressure pulses, the determined integral being proportional to the amplitude of the pulsatile pressure for the respective pulse; and using the time integral representations in the determination of the maximum value attained by the fluctuating component as the applied pressure is changed.

The present invention recognized that the signal from the pressure cuff, and more particularly the time dependent fluctuating component thereof representative of the pulsatile pressure within the blood vessel, may be differentiated to obtain the first time derivative of said fluctuating component. Further, it recognizes that this time derivative representation will cross a zero reference in the positive going direction at the time of end diastole and will return below the zero reference line when the systolic peak occurs at the end of the systolic rise. The invention further recognizes that the "above zero" area under the time derivative waveform is representative of the peak-to-peak (diastolic to systolic) amplitude of the respective blood pressure pulse and that such area may be determined by integrating the time derivative waveform over its "above zero" extent.

The present invention further recognizes that double differentiation of the cuff signal in the lower frequency range of the cuff pressure ramp aids in avoiding off-set of the fluctuating component derivative from the zero reference.

The method and apparatus of the invention additionally provide for integrating the time derivative representation when it crosses a reference magnitude, such as zero in a positive going direction and for terminating the integration when it crosses the reference in the negative going direction.

Still further, the invention provides for sampling and holding the integral value at the end of the period of integration and for clearing the integration means before an integration is undertaken in a subsequent blood pressure pulse.

It is thus, then, an object of the present invention to provide an improved apparatus and process/method for determining systolic pressure. Included in this object is the provision of an improved apparatus and process/method which determines systolic pressure with increased accuracy.

These and other objects and advantages of the present invention will be apparent to those skilled in the art after referral to the detailed description of the preferred embodiment in conjunction with the appended drawings.

BRIEF DESCRIPTION OF THE DRAWINGS

FIG. 1 illustrates a prior art technique for the determination of the peak-to-peak magnitude of the pulsatile pressure within a blood vessel;

FIG. 2 illustrates a technique for the determination of peak-to-peak amplitude of the pulsatile pressure in accordance with the invention;

FIG. 3A illustrates a typical oscillometric envelope of the pulsatile pressure of a blood vessel;

FIG. 3B illustrates the time derivative of the FIG. 3A waveform;

FIG. 3C illustrates a controlled mode timing diagram in accordance with the basic method and apparatus of the invention;

FIG. 3D illustrates the time intervals obtained from the waveform of FIG. 3B in accordance with the basic apparatus and process of the invention;

FIG. 5 illustrates a plot of the gain vs. frequency characteristics of a differentiating network employed in a preferred embodiment of the invention;

DETAILED DESCRIPTION OF THE PREFERRED EMBODIMENTS

Figure 4:
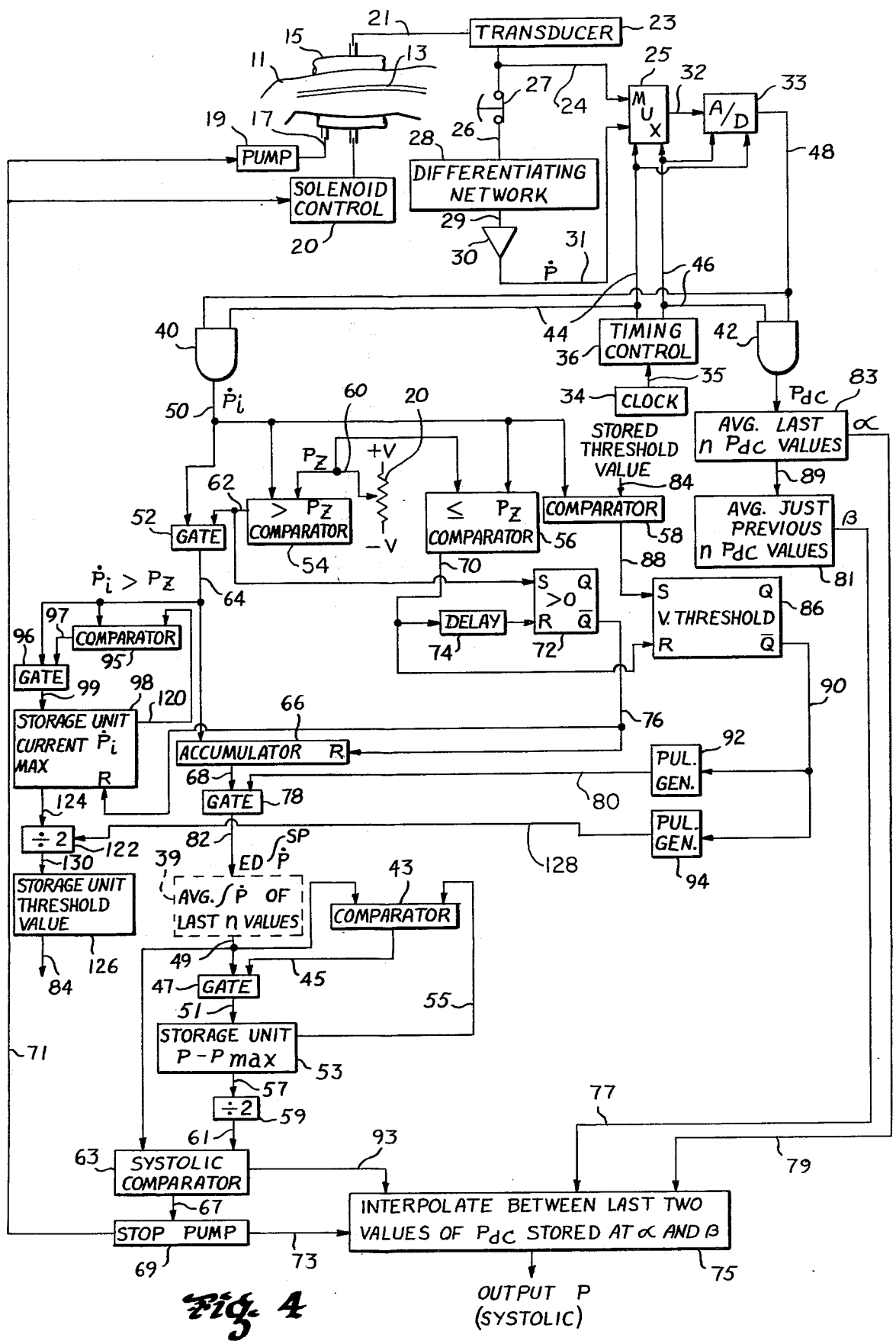
FIG. 4 illustrates, in a block diagram, the apparatus and process of one embodiment of the invention.

Referring first to FIG. 1, there is illustrated a functional block diagram of certain portions of the systolic pressure measuring apparatus described in the aforementioned application U.S. Ser. No. 578,047. More specifically, the functional blocks of FIG. 1 illustrate a filter network 100 having its output connected through amplifier 102 to the input of a peak-to-peak detector 104. Filter network 100 receives an input signal 106a on input conductor 106. The input signal 106a comprises a slowly-increasing ramp indicative of the applied cuff pressure and having superimposed thereon the time-dependent fluctuating component representative of pulsatile pressure within the blood vessel of the subject, which component representative of pulsatile pressure has a steeply rising wavefront relative to the remaining components during the rise from end diastole to systole. Filter network 100 was typically constructed such that its output waveform 100a had the linear effects of the pressure ramp removed therefrom, however, any random and uncontrollable deviation from the presumed linearity of the pressure ramp would introduce errors in the signal 100a. For instance, if a large perturbation in the cuff pressure ramp was encountered, filter 100 required a considerable time to recover and could allow some variation in the base line 100b (dotted) from which the fluctuating signal proportional to the amplitude of the pulsatile pressure within the blood vessel w as measured. Accordingly, each time peak-to-peak detector 104 is operated in response to sampling signals 108, the resulting output signal 110a appearing on conductor 110 included those peak-to-peak errors introduced by the variation in base line 100b.

In accordance with the present invention as illustrated generally in FIG. 2, an input signal 206a having a waveform identical to that of waveform 106a in FIG. 1 is applied to the input conductor 206 to differentiating network 200. Differentiating network 200 is constructed such that it provides single differentiation of signal 206a over that range of frequencies corresponding with the frequencies of the fluctuating signal proportional to the amplitude of the pulsatile pressure within the blood vessel, and doubly differentiates the input signal below that range of frequencies in order to remove the offset effects of a linear pressure ramp and any very low frequency perturbations which might have appeared in the otherwise linear pressure ramp.

A filter or differentiating network having the properties required of network 200 will possess the Gain v. Frequency characteristics illustrated in FIG. 5 in which the Gain curve exhibits a −6db per octave slope in the frequency range $f_1$-$f_2$ and a −12db slope for frequencies below $f_1$. The frequency range $f_1$-$f_2$ corresponds with the bandwidth of the $P_{ac}$ signal comprising the fluctuating quantity representative of the pulsatile pressure. That portion of input signal 206a representative of the pulsatile blood pressure is differentiated and appears at the output of differentiating network 200 as signal 200a, hereinafter designated $\dot{P}$.

This $\dot{P}$ signal (200a) is applied through amplifier 202 to the input of an integrator 204 which, by integrating the $\dot{P}$ signal over a predetermined interval during each pulse, provides an output value corresponding with the peak-to-peak pressure of each blood pressure pulse. Sample-and-hold circuitry 205 associated with integrator 204 serves to sample the value appearing at the output of integrator 204 at the end of each interval of integration and to hold that value for an interim period until integration of the next pressure pulse begins. Control of integrator 204 and sample-and-hold circuit 205 is provided by the RESET/INTEGRATE/HOLD-signal 208 which controls the period of integration and serves to clear the integrator prior to each new integration. The output from sample-and-hold circuit 205 appears on line 210 as waveform 210a having a magnitude which corresponds with the area under that portion of the waveform $\dot{P}$ being integrated.

Referring to FIGS. 3A and 3D for an understanding of the theory underlying the invention, it will be recalled from the aforementioned U.S. patent application Ser. No. 578,047 that the systolic pressure is equal to applied cuff pressure when the fluctuating quantity is about equal to one half the maximum of value of the fluctuating quantity. The maximum value of the fluctuating quantity is determined by measuring the diastole and systole in successive blood pressure pulses. That pulse exhibiting a maximum P-P amplitude is taken as the maximum value and the applied cuff pressure is further increased such that the P-P amplitude decreases and the systolic pressure is determined by noting the applied cuff pressure at which the P-P pressure becomes one half of the P-P maximum.

FIG. 3A illustrates the time-dependent fluctuating component, $P_{ac}$, representative of pulsatile pressure within a blood vessel. The root ED of each valley in the $P_{ac}$ waveform corresponds with the time of diastole, or more specifically end diastole in a heart beat and the waveform peak SP corresponds with the time of systole in the heart beat. As earlier described, the signal from the cuff is differentiated to remove the applied pressure ramp and low frequency random perturbations, and results in the derivative $\dot{P}$ of waveform $P_{ac}$, as represented in FIG. 3B. Because waveform $P_{ac}$ exhibits zero slope at both end diastole (ED) and the systolic peak (SP), the derivative waveform $\dot{P}$ will be of zero magnitude at each of those times. Further, because $P_{ac}$ exhibits a positive slope during the systolic rise between ED and SP, the $\dot{P}$ waveform lies above the zero reference line during this interval. The zero-crossing points ED and SP of the $\dot{P}$ waveform correspond with the points of maximum amplitude between successive $P_{ac}$ pulses and thus the area under the $\dot{P}$ waveform and above the zero reference between end diastole ED and the systolic peak SP provides a value which corresponds with the P-P value of the respective blood pressure pulse. This area is determined by integrating the "above zero" section of the $\dot{P}$ waveform. It should be noted that end diastole (ED) also corresponds essentially with the initiation of the rise to systolic peak (SP).

FIG. 3C illustrates a control signal generally similar to that of signal 208 in FIG. 2 which clears or resets the integrator prior to the interval of integration, then integrates the $\dot{P}$ signal over the interval of integration, and finally samples and holds the value of the integration as a representation of the P-P value of the respective blood pressure pulse This sequence of control events is repeated with the resetting operation being indicated by R, the integrating operation being represented by S, and the sample and hold operation being represented by S+H. In fact, the sampled integral may be held longer than is suggested by the brief duration of the S+H signal in FIG. 3C.

The results of integrating the $\dot{P}$ waveform between the limits of ED and SP are illustrated in FIG. 3D. The magnitude of the integral at the time of the systolic peak SP corresponds with the P-P value of the respective blood pressure pulse.

In implementing the concept of integrating the $\dot{P}$ waveform over the interval of systolic rise to obtain respective P-P values for the respective blood pressure pulses or heart beats, standard circuitry may be used to detect when the $\dot{P}$ waveform crosses the zero reference in the positive going direction to begin the integration and to determine when it crosses the zero reference in the negative going direction to terminate the integration and/or perform the sample and hold function. The integrator may be reset immediately after sample and hold and preferably continue until the next positive going zero-crossing of $\dot{P}$. The resulting integral may then be considered as representing the P-P value of the respective pulse. However, certain characteristics of the $P_{ac}$ waveform and/or the presence of signal artifacts during the diastolic drop may result in $\dot{P}$ appearing above the zero reference for a brief time other than between end diastole and the systolic peak. For instance, as illustrated in FIGS. 3A and 3B, if random muscular activity introduces a "high frequency" signal artifact (ART) just prior to end diastole when the slope of the $P_{ac}$ waveform is relatively flat, the derivative $\dot{P}$ waveform may present part of the artifact as a "greater than zero" value and result in the tentative values illustrated parenthetically in FIGS. 3C and 3D.

Figure 9:
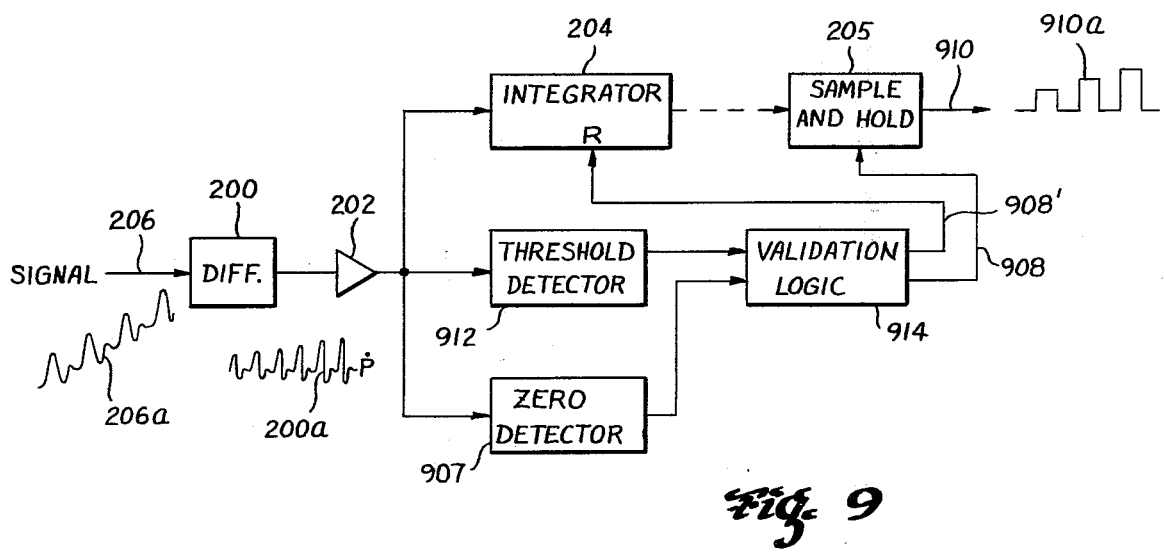
FIG. 9 illustrates a technique similar to that of FIG. 2 for the determination of peak-to-peak amplitude of the pulsatile pressure and further including threshold detection means for identifying particular "above zero" passages of the waveform derivative as valid systolic rises.

In accordance with an aspect of the invention, illustrated generally in FIG. 9, a threshold level is established for discriminating between those $\dot{P}$ values greater than zero which attend the systolic rise and those signals, such as artifacts and the like, which do not attend the systolic rise. The magnitude of $\dot{P}$ signal associated with the systolic rise is normally significantly greater than the magnitude of any other (above zero) portion of the signal (as from artifacts) and accordingly, this allows discrimination between such signals. The determination that the $\dot{P}$ waveform exceeds the threshold level during a particular "above zero" passage serves to validate the integration of that "above zero" passage between its respective ED and SP limits.

Referring to FIG. 9, in which those components functionally identical to corresponding components in FIG. 2 are identically numbered, the input signal 206a is differentiated by differentiating network 200 to provide the $\dot{P}$ waveform which is passed through amplifier 200 to the respective inputs of integrator 204, a threshold detector 912, and a zero-crossing detector 907. The zero-crossing detector 907 may correspond with means, not shown in FIG. 2, which established the interval of integration and resulted in the control signal 208 therein. The threshold detector 912 establishes a signal magnitude threshold value above which the $\dot{P}$ waveform is presumed to be indicative of a valid systolic rise. When the incoming $\dot{P}$ waveform exceeds the threshold level of detector 912, a signal is provided to the input of validating logic 914 indicative of such threshold level having been exceeded. Similarly, the validating logic 914 receives an input from the output of the zero-crossing detector 907 to define when the $\dot{P}$ waveform crosses a zero reference in the positive going direction and also in the negative going direction. The output 908' from validating logic 914 is applied to the RESET input of integrator 204 for resetting the integrator at least substantially at the beginning of each desired period of integration beginning with the $\dot{P}$ waveform crossing the zero reference in the positive going direction. The output 908 from validating logic 914 is applied to the "sample" input of the optional sample-and-hold circuit 205 and serves to store the integral value accumulated by integrator 204 between the positive going and negative going zero crossings of the $\dot{P}$ waveform only if threshold detector 912 has provided an indication that the $\dot{P}$ waveform during that interval was in fact a valid systolic rise. The output 910 of sample-and-hold circuit 205 varies from the output of 210 of FIG. 2 only where the latter might have included an invalid output value representative of a systolic rise when in fact only an artifact was present.

While a threshold of fixed magnitude above the zero reference might be utilized if an "above zero" portion of the $\dot{P}$ waveform did not vary in magnitude in successive pulses, such is not the case, particularly when using the present oscillometric blood pressure monitoring techniques in which the ac pressure signal $P_{ac}$ increases from a small amplitude at a low applied pressure to a large amplitude at a larger applied pressure and then to a smaller amplitude at a still larger applied pressure. Therefore, the threshold level, indicated as TRLD in FIG. 3B, is selected to be a function of the magnitude of the systolic rise portion of the $\dot{P}$ signal over one or more of the immediately preceding blood pressure pulsations. The increase (and subsequently decrease) in magnitude of successive systolic rises in the $\dot{P}$ waveform is sufficiently gradual, and the relative amplitude of any "above zero" non-systolic rise components of the $\dot{P}$ waveform are sufficiently small, that a dynamic threshold which corresponds with 50% of the maximum "above zero" amplitude of the systolic rise of the $\dot{P}$ waveform during the preceding pulse is herein considered sufficient for recognizing only those "above zero" portions of the $\dot{P}$ waveform which, in fact, attend the systolic rise.

It will be appreciated that the dynamic threshold level might be established by summing and weighting several prior systolic rise portions of the $\dot{P}$ waveform in which case threshold TRLD might be at a preselected level greater or less than 50% of the magnitude of the immediately preceding systolic rise. An analog example of a dynamic threshold detector of the type suitable for application herein is described in greater detail in U.S. Pat. No. 3,590,811 to Harris for Electrocardiographic R-wave Detector. Digital means for establishing a dynamic threshold level will be described hereinafter in greater detail.

Figure 6A:
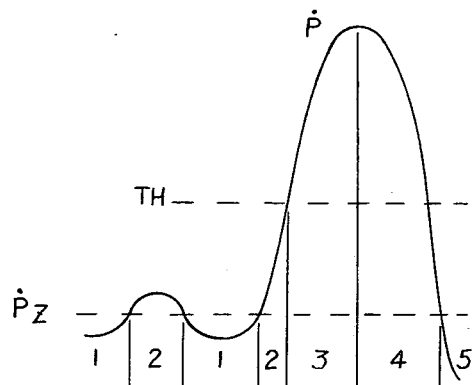
FIG. 6A represents an enlarged portion of the time derivative waveform illustrated in FIG. 3B showing a validation threshold level and the timing of various control states associated therewith in accordance with the embodiment illustrated in FIG. 4.
Figure 6B:
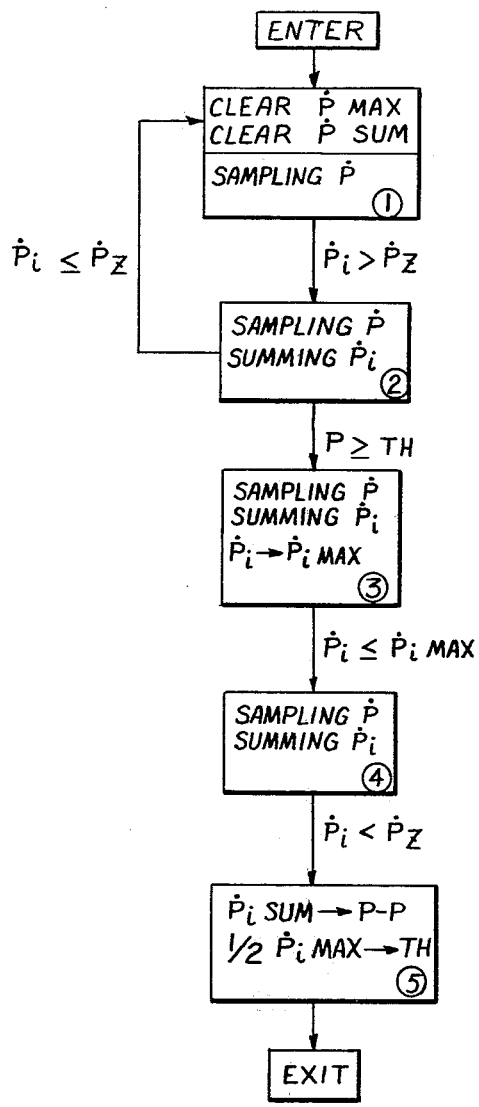
FIG. 6B illustrates a control state diagram in accordance with FIG. 6A and the embodiment of FIG. 4.
Figure 7:
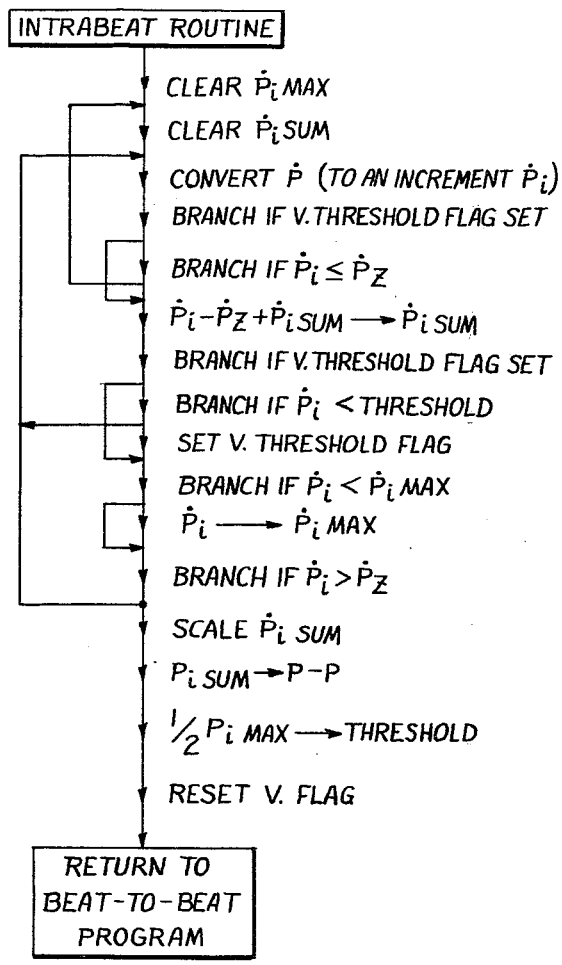
FIG. 7 illustrates a flow chart or decision tree of the control sequence employed by the embodiment illustrated in FIG. 4 between successive heart beats.

Reference is now made to FIGS. 4, 6, and 7 for a more detailed description of the apparatus and process of one aspect and embodiment of the invention. The apparatus is described with reference to the functional block diagram of FIG. 4 which provides for the digital processing of the analog signal received from transducer 23. However, it will be appreciated that analog implementation is similarly possible. More specifically, discrete electronic components, discrete digital chips, microprocessor technology and structure, or digital computer can be employed. FIGS. 6 and 7, respectively, comprise a state diagram and a flow chart, or decision tree, associated with the processing of the $\dot{P}$ signal between successive blood pressure pulses corresponding with successive beats of the heart. Generally speaking, the signal processing steps of the improved blood pressure monitoring apparatus and technique of the invention, illustrated in FIGS. 6 and 7, correspond with that portion of the FIG. 4 apparatus which integrates the $\dot{P}$ signal between the limits ED → SP.

The arm 11 of a test subject with artery 13 therein is surrounded by a typical blood pressure cuff 15. Typically, the brachial artery located in the upper arm is employed for this type of blood pressure measurement. Attached to the cuff via conduits 17 and 21 are pump 19 and pressure transducer 23, respectively. Transducer 23 has a transfer function such that its electrical output is substantially representative of its pressure input up to the limit of information contained in the pulse pressure. The pressure transducer serves to measure the pressure within the cuff, which pressure is the sum of pressure supplied by the pump and the fraction of pressure produced by blood pressure fluctuation within the artery, as represented by waveforms 106a and 206a in FIGS. 1 and 2, respectively. The fluctuating portion of the output of transducer 23 represents the amplitude of pulsatile pressure. The output of transducer 23 proceeds, as represented by line 24, to one input of multiplexing switch 25. The output of transducer 23 also proceeds, as represented by line 26, through normally closed switch 27 to the input of differentiating network 28. The output of differentiating network 28 proceeds, as represented by line 29, to amplifier 30 and proceeds as represented by line 31, to the other input of multiplexing switch 25.

The differentiating network 28 differentiates the input signal over the $f_1-f_2$ bandwidth of signal $P_{ac}$, as illustrated in FIG. 5, and additionally provides double differentiation of the frequencies below $f_1$. In this manner, substantially the only signal appearing on line 31 is that of the differentiated ($\dot{P}$) representation of the $P_{ac}$ waveform.

The output of multiplexing switch 25 proceeds, as represented by line 32, to analog-to-digital (A/D) converter 33. The output of A/D converter 33 proceeds, as represented by line 48, to inputs at gates 40 and 42, respectively. A clock 34 generates timing pulses which proceed, as represented by line 35, to a timing-control unit 36 which controls the switching of multiplexer 25, the conversion of the analog signal to a digital signal, and the gating of gates 40 and 42. One output of timing control 36 proceeds, as represented by line 44, to multiplexer 25, A/D converter 33, and the other input of gate 40 to control the conversion of the $\dot{P}$ signal appearing on line 31 to a digital form which is then applied to gate 40 via line 48. Another output of timing control unit 36 proceeds, as represented by line 46, to multiplexer 25, A/D converter 33, and the other input of gate 42 for controlling the conversion of the analog signal from transducer 23 to a digital form which is applied to the gate 42.

The gating signals appearing on lines 44 and 46, respectively connected to the inputs of gates 40 and 42, are of sufficient duration that the digitally-converted data associated therewith and appearing at the other input to the respective gate is passed through the particular gate. It will be further appreciated that the control signals represented by lines 44 and 46, as illustrated herein, exist mutually exclusively of one another such that the data appearing on line 31 or 24 is connected to the appropriate gate 40 or 42, respectively.

The period between successive blood pressure pulses is normally on the order of 800–1000 milliseconds with the systolic rise occupying some 10–20% of each period. The $\dot{P}$ signal may be integrated over the systolic rise portion by sampling a sufficient number of incremental portions ($\dot{P}_i$) of the $\dot{P}$ waveform to closely approximate the area under the $\dot{P}$ waveform. Typically, 10–20 samples during the 100–200 milliseconds of a typical systolic rise will be sufficient to provide the requisite number of $\dot{P}_i$ increments and the rate of clock 34 and the control signals on line 44 are selected accordingly. At least once during each blood pressure pulse a control signal appearing on line 46 operates to convert the signal on line 24 to digital form and to load the digitized signal into computing and averaging unit 83 as a measure of the applied pressure in cuff 15, as will be later described.

Each time a conversion and gating signal appears on line 44 from timing control unit 36, a correspondingly timed incremental sample $\dot{P}_i$ of the $\dot{P}$ waveform appears at the output of gate 40. This incremental sampling of the $\dot{P}$ waveform occurs preferably repetitively throughout the blood pressure pulse and at least during the interval in which the $\dot{P}$ waveform exceeds the zero reference level. The system timing also provides for sampling the waveform on line 24 at least once during each pressure pulse at a time (s) which does not conflict with the sampling of the $\dot{P}$ waveform on line 31.

Each sample $\dot{P}_i$ is supplied from gate 40, as represented by line 50, to respective inputs on gate 52, comparator 54, comparator 56 and comparator 58. The $\dot{P}_i$ input to comparator 54 is compared with a so-called zero reference value ($P_z$) represented as line 60. The output of comparator 54, as represented by line 62, is set to a level representative of unity if the $\dot{P}_i$ value appearing at the input of the comparator is greater than (>) the zero reference value $P_z$, and to a level representative of zero if it is equal to or less than $P_z$. The reference value $P_z$ appearing on line 60 is intended to correspond with the zero reference of FIG. 3B. The actual voltage appearing on line 60 is adjustable and appears as the voltage, for purposes of illustration, on the wiper of a potentiometer 20 having its end terminals connected to voltages respectively above and below a voltage which might correspond with the appropriate $P_z$ voltage. In order to accurately determine the correct $P_z$ voltage setting, switch 27 may be temporarily actuated such that a "zero" value appears as the $\dot{P}_i$ output from gate 40 on line 50, and the $P_z$ value on line 60 is adjusted to equal that appearing on line 50. It will be appreciated that the $P_z$ voltage level appearing on line 60 appears in a digital form (via A/D conversion means not shown) for comparison with the digitized $P_i$ value appearing on line 50.

Whenever the $\dot{P}_i$ value exceeds $P_z$, the unity output on line 62 enables gate 52 to pass the particular $\dot{P}_i$ value to the gate output, as represented by line 64. Accordingly, the data appearing on line 64 is representative of a $\dot{P}_i$ value greater than $P_z$.

Each such $\dot{P}_i$ value appearing on line 64 is applied to and accumulated in an accumulator 66 which, by summing successive increments $\dot{P}_i$, integrates the $\dot{P}$ waveform over the relevant interval from which incremental samples are taken. The accumulated sum of $\dot{P}_i$ increments is available at the output of accumulator 66 as represented by line 68 following the addition of each successive $\dot{P}_i$ increment to the sum. This output 68 from accumulator 66 is applied as an input to gate 78 for controlled introduction to the "beat-to-beat" circuitry to be hereinafter described.

The interval over which the accumulator 66 accumulates $\dot{P}_i$ increments is delimited at its later end by the $\dot{P}_i$ increment being equal to or less than ($\leq$) the zero reference value $P_z$. To identify this limit, the $\dot{P}_i$ value on line 50 and the $P_z$ value on line 60 are applied as the two inputs to comparator 56, the output being represented by line 70 and being set from a zero to a unity level when $\dot{P}_i$ is equal to or less than $P_z$.

A bistable element 72 has the output of comparator 54 appearing on line 62 extended to a "Set" input thereof for setting the Q output thereof to unity when $\dot{P}_i$ first exceeds $P_z$ and the output of comparator 54 goes from zero to unity. Similarly, the output of comparator 56 is applied on line 70 through delay element 74 to the "Reset" input of bistable element 72, such that the $\overline{Q}$ output of the bistable element is set from zero to unity substantially at the time $\dot{P}_i$ is no longer greater than zero. In this manner, the bistable element 72 serves to identify the interval during which the $\dot{P}_i$ increments of waveform $\dot{P}$ exceed $P_z$.

The $\overline{Q}$ output of bistable element 72 proceeds, as represented by line 76, to the "Reset" input of accumulator 66 for clearing or resetting the accumulator to zero when the $\overline{Q}$ output is unity. This resetting of accumulator 66 is intended to include not only the time at which the $\dot{P}_i$ waveform first moves to or below the $P_z$ reference level, but also through the time it remains at or below $P_z$. In this way, accumulator 66 is prevented from integrating any portion of the $\dot{P}$ waveform other than that which exceeds the $P_z$ reference level. Delay element 74, which may comprise a one-shot or the like, serves to briefly delay the resetting of bistable element 72 by an interval which is less than the interval between successive $\dot{P}_i$ samples but which is great enough to delay the resetting of accumulator 66 until the final integral value appearing on line 68 is transmitted through gate 78, as will be hereinafter explained.

A gating pulse appearing on line 80 is applied to gate 78 at the end of each systolic rise interval such that the time integral of the $\dot{P}$ waveform between the limits ED and SP appears at the output of the gate and proceeds, as represented by line 82, to the beat-to-beat signal processing circuitry. In order that the gating pulses appearing on line 80 are provided only at the end of systolic rise and not at the end of some other "above zero" portion of the $\dot{P}$ waveform which may be associated with the dicrotic notch or the like, the $\dot{P}_i$ increments appearing on line 50 are compared in comparator 58 with a stored threshold value appearing on line 84 to set a bistable element 86 if the threshold value is exceeded.

The stored threshold value appearing on line 84 is determined to be one half the magnitude of the $\dot{P}_i$ increment of maximum magnitude during the systolic rise of the preceding blood pressure pulse, as will be hereinafter described. the output from comparator 58 proceeds, as represented by line 88, to the "Set" input of bistable 86, and goes from zero to unity when the first $\dot{P}_i$ increment exceeding the stored threshold value occurs. This sets the Q output value of bistable 86 to the unity level, at which it remains until reset by a signal appearing on line 70 which is extended to the "Reset" input of the bistable element. The zero-to-unity signal transition on line 70 occurs when $\dot{P}_i$ is first $\leq P_z$. At this latter instant, the $\overline{Q}$ output of bistable 86 goes from zero-to-unity, which output proceeds as represented by line 90, to the inputs of pulse generators 92 and 94 respectively.

Pulse generator 92 is responsive to the zero-to-unity input transition for generating the output gating pulse represented by line 80 for passing the integral value appearing on line 68 through gate 78 to its output 82. It will be appreciated that the delay afforded by delay element 74 is sufficient to allow gating of the integral value on line 68 through gate 78 prior to the resetting of accumulator 66 by the "Reset" signal appearing on line 76.

Referring to the provision of a dynamic threshold value against which the $\dot{P}$ waveform is compared for the purpose of validating or rejecting in "above zero" passage of the waveform as a systolic rise, the signal on line 64 representative of $\dot{P}_i$ increments being $> P_z$ is extended to an input of comparator 95 and an input of gate 96. The comparator 95, as represented by line 97, controls gate 96. The gate 96 serves to allow selected $\dot{P}_i$ increments to be loaded into the storage unit 98 via line 99. The $\dot{P}_i$ value stored in storage unit 98 is applied, via line 120, to the other input of comparator 95. The output of comparator 95, as represented by line 97, goes from a zero level to a gate-enabling unity level whenever the incoming $\dot{P}_i$ increment is greater in magnitude than the $\dot{P}_i$ increment retained in storage unit 98. In this manner, the $\dot{P}_i$ increment retained in storage unit 98 represents the $\dot{P}_i$ increment of maximum magnitude to that time within the particular "above 0" portion of the $\dot{P}$ waveform.

At the time when the $\dot{P}$ waveform again crosses below the $P_z$ reference level, the value stored in unit 98 is representative of the maximum $\dot{P}_i$($\dot{P}_i$ max.) occurring during the immediately preceding "above zero" $\dot{P}$ waveform. The retained $\dot{P}_i$ max. value is applied to "divide-by-two" circuit 122 via line 124 to develop the threshold value which will be entered in storage unit 126. However, the actual division of the $\dot{P}_i$ max. value and its storage in unit 126 do not occur until receipt of a trigger or gating signal appearing on line 128 from the output of pulse generator 94. As with gating signal 80 from pulse generator 92, gating signal 128 occurs only if the present "above zero" passage of the $\dot{P}$ waveform has been recognized as a valid systolic rise following comparison with the threshold established by the preceding systolic rise, and it occurs at the time the $\dot{P}$ waveform passes below the $P_z$ reference level. At that time, the new $\dot{P}_i$max/2 value is entered, via line 130, in threshold storage unit 126 to become the new threshold value against which the next "above zero" passage of the $\dot{P}$ waveform is compared.

The "Reset" signal represented by line 76 is similarly extended to the "Rest" or clear input of storage unit 98 shortly after the new threshold value has been stored in unit 126 to clear storage unit 98. It will be appreciated that the resetting of $\dot{P}_i$ max storage unit 98 occurs not only when an "above zero" passage of the $\dot{P}$ waveform has been recognized as a systolic rise, but also following any other "above zero" passage of the $\dot{P}$ waveform, this latter operation being required to avoid the entry of an artifact $\dot{P}_i$ value in the determination of $\dot{P}_i$ max and the development of a new threshold value.

Referring now to the value represented by line 82 which comprises the time integral of the $\dot{P}$ waveform between the limits ED-SP, such value is available at the conclusion of each respective systolic rise for application to the beat-to-beat circuitry described in the aforementioned U.S. Patent Application Ser. No. 578,047. Briefly, the $\dot{P}$ time integral quantity appearing on line 82 proceeds through an optional averaging unit 39 (represented by dotted lines) which may average several successive blood pressure pulses, e.g. four, and thence, as represented by line 49 to inputs of comparator 43, gate 47 and systolic comparator 63 respectively. The comparator 43, as represented by line 45, controls gate 47. The gate 47 serves to allow the averaging unit 39, as represented by line 49, to load the selected value of the (possibly averaged) $\dot{P}$ systolic rise integral representative of the pulse P-P value, as represented by line 51, into storing unit 53.

The value of the quantity being stored in storing 53 is supplied to the comparator 43, as represented by line 55. Within comparator 43, stored previous representations of the tentative maximum value of the $\dot{P}$ systolic rise integral are compared with current values of said quantity introduced into the comparator 43 as represented by line 49. Where the value of said quantity supplied to the comparator 43 by line 49 is greater than the quantity tentatively stored in the storage unit 53, as applied to the comparator 43 by line 55, then gate 47 is activated by the comparator 43 via line 45 and the larger value of said quantity replaces the tentative maximum value in storage unit 53.

The tentative maximum value of said P-P quantity is introduced, as represented by line 57, into a halving unit (divide by two) 59 wherein it is divided in half. The divided-in-half value is introduced, as represented by line 61, to systolic comparator 63. The (now) current value of the (possibly averaged) P systolic rise interval is supplied to systolic comparator 63 by line 49. When systolic comparator 63 determines that the quantity being supplied thereto by line 49 is less than or equal to one half of the tentative maximum value being applied thereto by line 61, the systolic comparator 63 orders, as represented by line 67, the switching means 69 to stop the pump 19 and bleed the cuff 15 through solenoid control valve conduit 20, the stop and bleed order being represented by line 71.

The switching means 69, as represented by line 73, and systolic comparators 63 as represented by line 93, also order interpolating unit 75 to interpolate between the values of the applied pressure, that is, pressure being applied to cuff 15 by pump 19, so as to determine the precise applied pressure corresponding to said quantity (P-P) being about one half of said maximum value.

Values of applied pressure are supplied to interpolation unit 75, as represented by line 77 and 79. Line 77 represents introduction of the applied pressure value for measurement just before the quantity became less than one half the maximum value, and line 79 represents applied pressure when the quantity was equal to or slightly less than one half the maximum value. Stated another way, line 79 represents the more recent value of applied pressure. These values of applied pressure are obtained by introducing the digitized waveform of line 24 from transducer 23 through gate 42 to a "last" (most recent) storage unit 83 which averages the signal over the last "n" (e.g. four) most recent blood pressure pulses. As each new blood pressure pulse occurs, the average value appearing in averaging and storing unit 83 is updated with the immediately preceding average proceeding, as represented by line 89, to the storage unit 81 which then stores the "just previous" average value.

It will usually suffice for the analog signal on line 24 to be converted to its digital value substantially at the time of the systolic peak SP, as for instance by utilizing the signal on line 90 from bistable 86 as a timing input to timing control unit 36. Essentially, the analog signal appearing on line 24, and ultimately in digitized form on line 48, is principally comprised of the slowly increasing pressure ramp with but a very small fluctuating quantity representative of the pulsatile pressure superimposed thereon. Accordingly, the value appearing on line 24 is substantially proportional to the pressure applied by cuff 15 and represented as $P_{dc}$; however, low pass filter means may be introduced to line 24 if it is desirable to remove the pulsatile component therefrom.

Certain obvious aspects and controls of the circuit embodiment illustrated in FIG. 4 have been omitted from specific illustration therein and include, for instance, an initializing signal applied when operation of pump 19 is initiated to clear and/or reset essentially all of the storage elements to an appropriate initial state. Normally this initial state is representative of a "zero" condition. It may be desirable, however, to initially store some non-zero minimum threshold value in the threshold value storage unit 126 such that the systolic rise validation procedure is operative with the very first blood pressure pulse.

Further, the systolic rise portion of the $\dot{P}$ waveform might be integrated over somewhat greater or lesser limits than the preferred ED-SP limits to obtain a value which is generally representative of the P-P value of the respective blood pressure pulse. In such instance, the so called $P_z$ reference appearing on line 60 and utilized by the various comparators might assume a value slightly above or below zero.

Still further, although $\dot{P}_i$ max was divided by two, it will be appreciated that another appropriate divisor of nearly the same value might be used if the cuff 15 and/or the patient's arm are structured such that the cuff applies maximum pressure to one side or the other of the normal position mid-length of the cuff.

Further still, the illustration of FIG. 4, particularly as regards the digitalization of the $\dot{P}$ waveform, the determination of the limits of the systolic rise, and the determination of a valid systolic rise, is intended to portray but one of several possible alternatives circuitry configurations for implementing the principles of the invention. For instance, the determination of when the $\dot{P}$ waveform goes above and below $P_z$ and whether or not a valid systolic rise has occurred might be made on the analog $\dot{P}$ waveform prior to its digitalization, and such determinations then used to control which portions of the $\dot{P}$ waveform appear as $\dot{P}_i$ increments for introduction to accumulator 66. Further, comparator 56 and "state-indicating" bistables 72 and 86 might be omitted if comparators 54 and 58 operate only on analog waveforms or otherwise have the digital signal information continuously applied thereto.

It is understood by those skilled in the art that implementation of the various functions represented in FIG. 4 is accomplished from commercially available component parts. Other than the pneumatics, pneumatic controls and initial analog circuitry associated with transducer 23, the remaining functional blocks are constructed primarily from commercially available microprocessors and other digital circuitry. In fact, there follows a brief description of a state diagram illustrated in FIG. 6B and associated with the waveform shown in FIG. 6a, and a flow chart or decision tree illustrated in FIG. 7 for clearly setting forth the decisional and operational sequence employed between successive blood pressure pulses or heart beats.

FIG. 6A illustrates a portion of the $\dot{P}$ waveform and subdivides the waveform according to time into five different states as associated with the signal processing state diagram appearing in FIG. 6B. The state diagram and the more detailed decision tree of FIG. 7 which derives therefrom, provide sufficient information for one of ordinary skill in the art to implement the concepts of the invention in a digital manner, as with microprocessors.

Referring to FIG. 7 and the sequence of instruction which it provides, between the systolic peak (SP) and end diastole (ED) of the preceding blood pressure pulse, and thus prior to the initiation of the systolic rise of the current pressure pulse, the storage unit (98) containing $\dot{P}_i$ max is cleared and the storage unit (accumulator 66) containing $\dot{P}_i$ sum (i.e. $\int_{ED}^{SP} \dot{P}$)

is next cleared also. Then, a brief time-increment of the $\dot{P}$ waveform is converted to a digital value represented by $\dot{P}_i$ which indicates the magnitude of the particular increment. Assuming for the moment that the system is in State "one" or possibly "two", of waveform $\dot{P}$, then $\dot{P}_i$ is compared with $\dot{P}_z$. If $\dot{P}_i$ is less than or equal to $\dot{P}_z$, the system remains in State "one" and the sequence returns to the "clear $\dot{P}_i$ sum" step and is repeated. If, on the other hand, $\dot{P}_i$ is greater than $\dot{P}_z$, State "two" is entered and the magnitude of $\dot{P}_i$ above the reference $\dot{P}_z$ is added to the sum of $\dot{P}_i$ increments (in accumulator 66) and thereby increase the value of $\dot{P}_i$ sum.

Next, a determination is made as to whether or not a valid systolic rise has been recognized by the setting of a "V. Threshold Flag". Assuming the "V, Flag" has not yet been set, as will be the case until State "three" of FIG. 6A and 6B is entered, the sequence then considers whether $\dot{P}_i$ is less than the threshold. Because the system is still in State "two", the program will branch and the sequence beginning with the conversion of the next increment of the $\dot{P}$ waveform to a $\dot{P}_i$ will be repeated. The sequence of State "two" continues until $\dot{P}_i$ is ≥ the threshold level at which time the "Threshold Flag" is set and the transition from State "two" to State "three" occurs.

The sequence then determines whether or not the particular $\dot{P}_i$ is less than a stored value $\dot{P}$ max. Inasmuch as $\dot{P}_i$ max is determined by the maximum preceding $\dot{P}_i$ increment, a new $\dot{P}_i$ will not normally be less than $\dot{P}_i$ max throughout State "three". Thus, the sequence provides for the current value of $\dot{P}_i$ to be loaded into the $\dot{P}_i$ max storage position to create a new $\dot{P}$ max.

The sequence then determines whether or not $\dot{P}_i$ is greater than $\dot{P}_z$. Assuming that $\dot{P}_i$ is in either State "three" or State "four", it will be larger than $\dot{P}_z$ and, accordingly, the sequence returns to the step at which the $\dot{P}$ waveform is converted to a new $\dot{P}_i$ increment and the sequence is repeated. In this manner, $\dot{P}_i$ increments are continually added to the stored $\dot{P}_i$ sum throughout States "three" and "four" as well as State "two".

When the $\dot{P}$ waveform peak is reached, at the transition from State "three" to State "four", a maximum $\dot{P}_i$ will occur and each subsequent $\dot{P}_i$ will normally be smaller in value than the $\dot{P}_i$ max which was retained in storage at the peak. Accordingly, the sequence branches around the step which otherwise would enter the value of the now smaller $\dot{P}_i$ into the $\dot{P}_i$ max storage.

The transition from State "four" to State "five" a new $\dot{P}_i$ is no longer greater than $\dot{P}_z$ and the sequence recognizes that the integration has been completed and the $\dot{P}_i$ may then be scaled as required. The scaled $\dot{P}_i$ sum is stored in a position representative of the peak-to-peak(P-P) magnitude of the respective blood pressure pulse for use in the interbeat processing.

Finally, the value previously stored in $\dot{P}_i$ max is halved and that value is stored in a position representative of the threshold value to establish the threshold for the succeeding pulse. It will be appreciated that the threshold value will increase as the magnitude of the ultimate $\dot{P}_i$ max in each pulse increases, and will similarly decrease as that ultimate $\dot{P}_i$ max values decrease. The "V. Threshold Flag", which will have been previously set, is reset either now at the end of the present sequence or alternatively at the initiation of the sequence in the sequence in the next blood pressure pulse.

It will be noted that if a particular State "two" never does attain the threshold level (State "three") before dropping below $\dot{P}_z$, (as in the case of an artifact), the "V. Threshold Flag" will remain in its reset state. Although $\dot{P}_i$ increments are continually added to $\dot{P}_i$ sum during this State "two" interval, they are not subsequently treated as a valid value because the "V. Threshold Flag" is not yet set and the sequence branches back to the "clear $\dot{P}_i$ sum" step while the waveform is below $\dot{P}_z$ to continually clear the $\dot{P}_i$ sum storage element.

Figure 8:
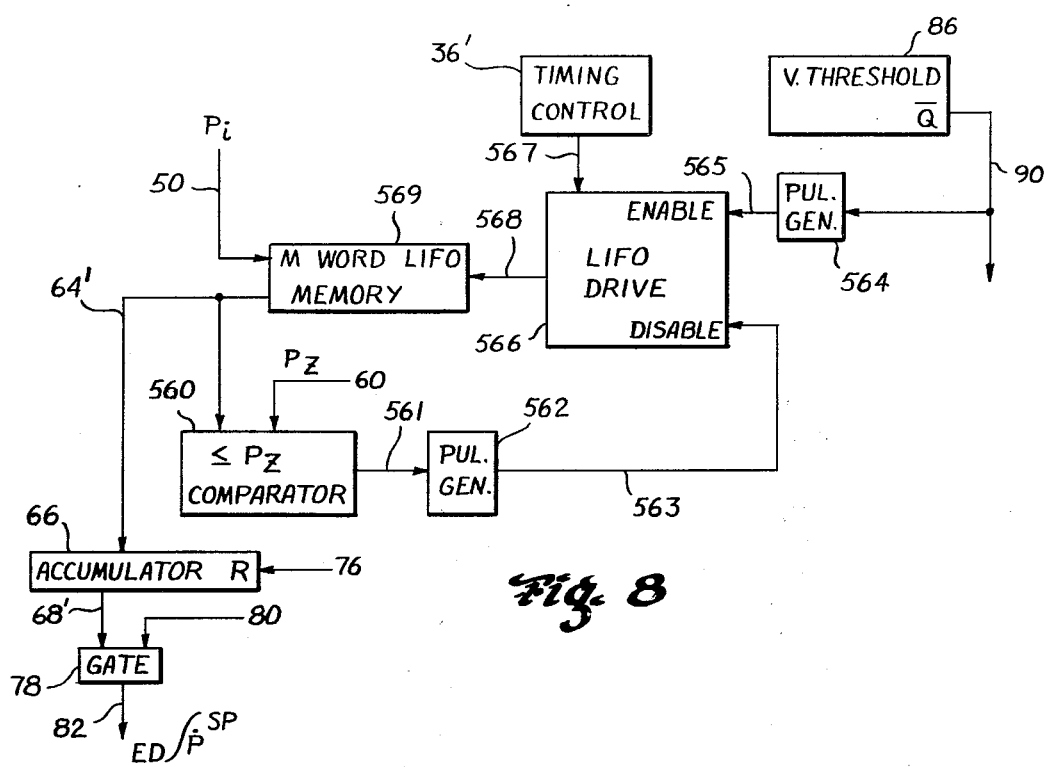
FIG. 8 illustrates, in an abbreviated block diagram supplemented by FIG. 4, the apparatus and process of another embodiment of the invention.

Referring to FIG. 8 there is illustrated an alternate embodiment of the invention in which it may be desirable to store a greater portion of the $\dot{P}$ waveform than is represented by a single $\dot{P}_i$ increment. In such a system the integration of the appropriate intervals of the $\dot{P}$ waveform may be accomplished by reading the above-zero $\dot{P}_i$ data stored in memory backwardly out of the memory and into integrating means, such as the accumulator 66 of FIG. 4, from which it is then processed in the same manner as that described with reference to FIG. 4. Those elements of the embodiment of FIG. 4 which are in common with the elements of the embodiment of FIG. 8 and which do not contribute to an understanding of the latter are omitted from illustration in FIG. 8. Similarly, those elements and functions in the embodiment of FIG. 4 which are identical in the embodiment of FIG. 8 are similarly numbered in FIG. 8.

The $\dot{P}_i$ increments 50 are extended to the forward input of a last-in-first-out (LIFO) storage element or memory 569. Memory 569 has a word length of "m" units where "m" corresponds with the number of $\dot{P}_i$ increments that would occur during a systolic rise of maximum anticipated duration (ie. slowest anticipated pulse rate). This may comprise some twenty to twenty-five $\dot{P}_i$ increments. The zero crossing and threshold detecting circuitry of FIG. 4 operate to drive the $\overline{Q}$ output of bistable 86 to unity at the instant the $\dot{P}$ waveform goes equal to or below zero, assuming the threshold level has been exceeded. This positive transition of the $\overline{Q}$ output of bistable 86 appears on line 90 and is extended as an input to pulse generator 564 which in turn provides a pulse output on line 565 extended to the ENABLE input of LIFO drive circuitry 566. The LIFO drive circuitry 566 receives an input from timing control circuitry 36' via line 567 and is operative, when enabled, to provide reverse drive pulses to the LIFO memory 569. The reverse drive pulses cause the $\dot{P}_i$ data stored in LIFO memory 569 to be read out therefrom on line 64' in the reverse order from that in which it was entered. Timing control 36' may provide drive pulses at a sufficient $f$ rate for the entire contents of memory 569 to be reversely read between successive entries of new $\dot{P}_i$ increments. However, if the rate of drive pulses from timing control 36' is slower, it may then be necessary to inhibit the input of new $\dot{P}_i$ increments 50 to memory 569 during the LIFO read out.

The $\dot{P}_i$ increment which resulted in the positive going transition of the $\overline{Q}$ output of bistable 86 is not itself stored in memory 569 and accordingly, the last $\dot{P}_i$ increment entered will be of a small positive value. Thus, when the contents of memory 569 are read in reverse order, the data appearing on line 64' will first be of a small positive value and will increase in the positive direction and then decrease toward the zero reference, in the reverse sequence from that in which it was initially stored. Line 64' comprises one input to a comparator 560, the other input of which is the $P_z$ reference 60. Comparator 560 goes from zero to unity when the data appearing on line 64' is equal to or goes less than the $P_z$ reference. The output of comparator 560 is extended via line 561 to the input of a pulse generator 562 for generating an output pulse when the comparator makes a transition from zero to unity. The output of pulse generator 562 is extended via line 563 to the DISABLE input of the LIFO drive control circuitry 566 for inhibiting further application of reverse drive pulses to the LIFO memory 569. In this way, the $\dot{P}_i$ data appearing on line 64' is the time-reversed, above-zero data representative of a valid systolic rise for a blood pressure pulse.

The data on line 64' is extended to the accumulator 66 wherein it is summed as earlier described. The output of accumulator 66 is extended via line 68' to the input of gate 78. Control pulse 80 applied to gate 78 serves to pass the resultant sum accumulated in accumulator 66 through gate 78 to its output, represented by line 82, and subsequently to the processing circuitry (not shown) described earlier with reference to FIG. 4.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. In an apparatus for determining systolic pressure of a living test subject, said apparatus including means for applying a selectively changeable pressure to the test subject adjacent a blood vessel, means for measuring a fluctuating quantity proportional to a sum, said sum comprising a time-dependent fluctuating component proportional to the amplitude of the pulsatile pressure within the blood vessel plus the selectively changeable pressure applied externally adjacent the blood vessel, means for determining the maximum value attained by said fluctuating component as the applied pressure is changed, means for storing a representation of said maximum value, means for determining when said fluctuating component is substantially equal to about one half of said maximum value for an applied pressure greater than the pressure applied when said maximum value results, and means for reading out said applied pressure corresponding to said fluctuating component being substantially equal to a predetermined fraction of said maximum value, said readout pressure corresponding to the systolic pressure of said subject, the improvement comprising:

means for converting said quantity into a representation of a time derivative of said fluctuating component thereof; means for obtaining the time integral of said time derivative representation over an interval of predetermined limits in each of successive blood pressure pulses, said interval of integration extending substantially from the initiation of systolic rise to the systolic peak in respective blood pressure pulses, each said integral being proportional to the amplitude of said pulsatile pressure for the respective pulse; and means for extending said time integral representations to said maximum value determining means.

2. The apparatus of claim 1 wherein said time integral obtaining means comprise
resettable integrating means;
means responsive to said time derivative representation for resetting said integrating means to an initial condition;
means responsive to said time derivative representation for initiating integration of said time derivative representation at a selected initiation time; and
means responsive to said time derivative representation for sampling the integral value accumulated by said integrating means at a selected sampling time for extension to said maximum value determination means.

3. The apparatus of claim 2 wherein said time derivative representation crosses a reference magnitude in one direction at said initiation of systolic rise and crosses said reference magnitude in the opposite direction at said systolic peak, said integration initiating means and said sampling means being responsive to said time derivative representation crossing said reference magnitude in said first and said opposite directions, respectively, for initiating said integration and sampling the integrated value, respectively.

4. The apparatus of claim 3 wherein said resetting means is responsive to said time derivative representation for resetting said integrating means when said time derivative representation is to said opposite direction from said reference magnitude.

5. The apparatus of claim 4 wherein said resetting means discontinues said resetting of said integrating means substantially at the time said integration is initiated.

6. The apparatus of claim 5 wherein said reference magnitude is substantially zero and the magnitude of said time derivative representation is greater than zero during systolic rise.

7. The apparatus of claim 2 including means for converting said time derivative representation to consecutively-timed increments, said consecutively-timed increments being extended to said integrating means for said integration therein.

8. The apparatus of claim 1 wherein said quantity converting means comprises a differentiating network for converting said quantity into a representation of the first time derivative thereof over the frequency band of said fluctuating component and for converting said quantity into a representation of the second time derivative thereof at the lower frequency of said selectively changeable pressure.

9. In a method for determining systolic pressure of a living test subject, including the steps comprising:
applying a selectively changeable pressure to the test subject adjacent the blood vessel;
measuring a quantity proportional to a sum, the sum comprising a time dependent fluctuating component proportional to the amplitude of the pulsatile pressure within the blood vessel plus the selectively changeable pressure applied externally adjacent the blood vessel;
determining the maximum value attained by the fluctuating component as the applied pressure is changed;
storing a representation of said maximum value;
determining when said fluctuating component is substantially equal to a predetermined fraction of said maximum value for an applied pressure greater than the pressure applied when said maximum value results; and reading out the applied pressure corresponding to said fluctuating component being substantially equal to about one half of said maximum value, said readout pressure corresponding to the systolic pressure of said subject, the improvement comprising the steps of:

converting said quantity proportional to said sum into a representation of a time derivative of said fluctuating component thereof;

determining the time integral of said time derivative representation over an interval of predetermined limits in each of successive blood pressure pulses, said predetermined interval of integration extending substantially from the initiation of systolic rise to the systolic peak in respective blood pressure pulses, whereby the determined integral is proportional to the amplitude of the pulsatile pressure for the respective pulse; and using said time integral representations in said determination of the maximum value attained by said fluctuating component as the applied pressure is changed.

* * * * *